United States Patent [19]
Sherman et al.

[11] Patent Number: 5,643,264
[45] Date of Patent: Jul. 1, 1997

[54] ILIAC SCREW

[75] Inventors: Michael C. Sherman, Memphis; Eddie Ray, III, Cordova, both of Tenn.; Jean Pierre Farcy, Piermont, N.Y.; Joseph Tai, Memphis, Tenn.

[73] Assignee: Danek Medical, Inc., Memphis, Tenn.

[21] Appl. No.: 527,415

[22] Filed: Sep. 13, 1995

[51] Int. Cl.$^6$ .................................................. A61B 17/56
[52] U.S. Cl. .................... 606/61; 606/73; 606/72; 606/70
[58] Field of Search ................... 606/60, 61, 69, 606/70, 71, 72, 73

[56] References Cited

U.S. PATENT DOCUMENTS

| | | | |
|---|---|---|---|
| 2,081,293 | 11/1937 | Davis | 606/73 |
| 4,978,350 | 12/1990 | Wagenknecht | 606/73 |
| 5,217,462 | 6/1993 | Asnis et al. | 606/73 |
| 5,261,909 | 11/1993 | Sutterlin et al. | 606/61 |
| 5,300,076 | 4/1994 | Leriche | 606/73 |
| 5,330,473 | 7/1994 | Howland | 606/61 |
| 5,360,448 | 11/1994 | Thramann | 606/73 |
| 5,375,956 | 12/1994 | Pennig | 606/73 |

OTHER PUBLICATIONS

*Isola Spinal System Brochure,*: AcroMed Corp; pp. 1-2, Sep. 1993.

*Primary Examiner*—Michael Buiz
*Assistant Examiner*—Mark S. Leonardo
*Attorney, Agent, or Firm*—Woodard, Emhardt, Naughton, Moriarty & McNett

[57] ABSTRACT

An iliac screw includes a smooth distal shank (35), a threaded proximal shank (37) and a proximal head portion (38). The smooth distal shank (35) is configured to penetrate the cancellous bone of the iliac wings, while the threaded shank (37) carries bone threads configured for engagement with the cortical or the cancellous bone. The head portion (38) is configured for engagement with an elongated fixation member, such as a spinal rod.

19 Claims, 4 Drawing Sheets

ILIAC SCREW

BACKGROUND OF THE INVENTION

The present invention broadly concerns devices and systems for use in the fixation of the spine and correction of spinal disorders. In one aspect, the invention concerns a bone engaging element for use in a spinal implant construct utilizing elongated fixation elements, such as spinal rods, contoured for connection at various locations along the length of the spinal column. More specifically, the invention concerns a screw for anchoring the spinal rods of the construct to the iliac wings or the pelvis.

Several techniques and systems have been developed for use in correcting spinal injuries and deformities, stabilizing spinal curves and facilitating spinal fusion. Frequently, an elongated spinal member, such as a bendable rod, is longitudinally disposed adjacent the vertebral column and is fixed to various vertebrae along the length of the column. This fixation is achieved by a number of fixation elements, which can be hooks or bone screws of various configurations.

An example of one such system is the TSRH® spinal system of Danek Medical, Inc. In one construct using the TSRH® system, shown in FIG. 1, a fixation construct 10 includes two elongated rods 11 disposed adjacent the spine on opposite sides of the spinous process. In the illustrated construct, the rod is shown extending from the thoracic vertebrae to the sacrum and pelvis. It is of course known that fixation along the entire length of the spine up to the cervical vertebrae can also be accomplished using a rod system such as the TSRH® system.

In this system 10, a variety of bone engaging fasteners 15 are engaged to the rods 11 by way of eyebolt assemblies 16. These eyebolt assemblies are known components of the TSRH® system and are particularly distinguished for the "three-point shear clamp" effect achieved by the eyebolt assemblies to clamp the bone engaging fasteners 15 to the spinal rods 11.

In many spinal instrumentations, the inferior ends 11a of the spinal rods 11 are anchored to either the sacrum or the pelvis. In FIG. 1, the spinal fixation system 10 is anchored to the iliac wings I according to the Galveston fixation technique. In accordance with this technique, a Galveston rod segment 12 is linked to the ends 11a of the spinal rods 11. The Galveston rod segments 12 each include an iliac extension 13 which is engaged within holes bored through the iliac wings I. A transverse plate 17, preferably the Crosslink® plate provided by Danek Medical, Inc., is engaged between the two Galveston rod segments 12 by way of separate eyebolt assemblies 18.

This particular Galveston fixation technique permits correction of pelvic obliquities. Perhaps more importantly, the Galveston approach provides a solid anchor for the superior fixation construct. The iliac wings have large bony regions for significant purchase of the Galveston rod segments 12. These rods and specifically the iliac extensions 13, can have a length of 85–100 mm to provide a substantial moment arm to react the large loads generated by the entire construct. The Galveston rods provide a very stable foundation for fusion at superior vertebral levels.

In the construct depicted in FIG. 1, the Galveston rod segments 12 are engaged to the spinal rods 11 by way of a pair of offset plates 20. These offset plates 20 are engaged to the respective rods by way of eyebolt assemblies 21. This offset plate 20 allows separate rods to be linked axially. This particular configuration has replaced the more complex technique in which the spinal rod itself was bent at its inferior end to engage the iliac wings I. In other words, this technique allows the substitution of a much shorter rod segment 12 already carrying the Galveston bend 14, thereby permitting ready engagement between the iliac wings and the spinal rods 11. The addition of the Crosslink® transverse plate 17 adds greater strength and rigidity to the construct and prevents pullout of the iliac extensions 13 from the iliac wings I.

Although the use of the offset plates 20 has greatly simplified anchoring to the iliac bone from the prior Galveston technique, there still is room for improvement. In particular, the shorter rod segments 12 depicted in FIG. 1 still require the Galveston bend 14 for the iliac extensions 13. It is a known principal of mechanical engineering that bends in the rods yield stress concentrations and can also produce asymmetric loading of the fixation construct. It is desirable to engage the bones of the sacrum or ilium without the requirement for bending the rods. In order to achieve this capability, a novel spinal fixation system 25 has been developed, as illustrated in FIG. 2. In this fixation construct 25, the spinal rods 11 and bone engaging fasteners 15 are identical to the similar components in the construct 10 shown in FIG. 1. The difference is that the Galveston rod segments 12 and offset plates 20 have been replaced by extension rod assemblies 27. The extension rods assemblies 27 include an extension rod 28 having a rod portion 29 and a head portion 30. The extension rods 28 are engaged to the inferior ends 11a of the spinal rods 11 by way of clamping members 31. The details of this variable angle extension rod assembly 27 are set forth in a co-pending commonly-owned patent application entitled "VARIABLE ANGLE EXTENSION ROD" filed in the name of inventors Sherman and Tai on Sep. 13, 1995. The disclosure of this application as it pertains to the details of the extension rod assembly 27 are incorporated herein by reference.

As discussed more fully in that co-pending application, the extension rod assembly 27 eliminates the need for the Galveston bends and instead provides two angular and one translational degrees of freedom to interconnect the spinal rods 11 to bone screws, such as bone screw 33 engaged in the iliac wings I.

In the construct 25 depicted in FIG. 2, the screws 33 are engaged to the extension rods 28 by way of clamping assemblies 34. As thus far described, the construct 25 of FIG. 2 can utilize a wide range of screws for engaging the iliac wings I. One option is to use the variable angle screw disclosed in U.S. Pat. No. 5,261,909 in the name of inventors Sutterlin and Sherman. This '909 patent, which is assigned to the owner of the present invention, discloses a variable angle clamping mechanism for engaging a bone screw to an elongated rod at variable angular positions in two degrees of freedom. Specifically, the variable angle clamping mechanism can be rotated around the longitudinal axis of the elongated rod. In addition, the head of the bone screw can be rotated relative to the clamping mechanism to achieve a plurality of different angular positions.

While this variable angle screw provides adequate fixation into the iliac bone, its insertion into the bone is rendered difficult because the bone screw is fully threaded. On the other hand, the use of a smooth Galveston rod, as is known in the art, can lead to a "windshield wiper effect" in which cyclic loads applied to the construct 25 gradually cause the Galveston rod to erode or whittle away at the bone opening in the iliac wing I. While the Galveston rod provides a very long moment arm for securing the base of the spinal construct, this same long moment arm can lead to loosening of the rod. On the other hand, while the variable angle screw described above can obtain a secure fixation resistant to pull-out from the iliac wings, it is not readily capable of achieving the long moment arms of the Galveston rod.

A need has remained for an iliac bone fixation member that combines the benefits of the threaded variable angle screw with the benefits of the smooth Galveston rod without the corresponding disadvantages.

SUMMARY OF THE INVENTION

In order to address these needs, a novel iliac screw is provided which can be engaged to elongated spinal elements, such as an elongated spinal rod or a Galveston rod segment. Specifically, in accordance with the invention the iliac screw can have a length approximating the length of a typical Galveston rod segment, namely in the range of 85–100 mm, for deep penetration into the iliac bone. In a unique aspect of this iliac screw the distal shank portion of the screw is unthreaded or smooth, while the proximal portion of the shank bears bone engaging threads. The proximal threaded portion of the shank carries threads that are configured for engaging either cortical or cancellous bone. Preferably, the threads are long enough to engage the cortical bone and extend a significant amount into the cancellous bone. On the other hand, the proximal threaded portion is not so long as to present difficulties in implanting the iliac screw into the iliac wing.

In a further aspect of the invention, the iliac screw includes a head portion that is adapted to engage a spinal rod. In one preferred embodiment, this head portion includes variable angle features to permit connection to the spinal rod in variable angular orientations. A variable angle clamping device then can be used to engage the iliac screw to a spinal rod or Galveston rod segment. This permits the iliac screw to achieve whatever orientation is necessary to be fully disposed within the iliac wing, thereby enhancing the fixation and anchoring of the spinal construct.

It is one object of the present invention to provide an iliac screw that combines the benefits of a fully threaded screw with the benefits of a long Galveston rod. It is further an object of the invention to provide such a screw than can be readily engaged to an elongated rod or other elongated fixation member.

A further object is contemplated by aspects of the iliac screw that permit engagement to the elongated fixation member at variable angular orientations, particularly in multiple angular degrees of freedom. Other objects and benefits of the present invention will become apparent upon consideration of the following disclosure and accompanying figures.

DESCRIPTION OF THE PREFERRED EMBODIMENTS

Figure 1:
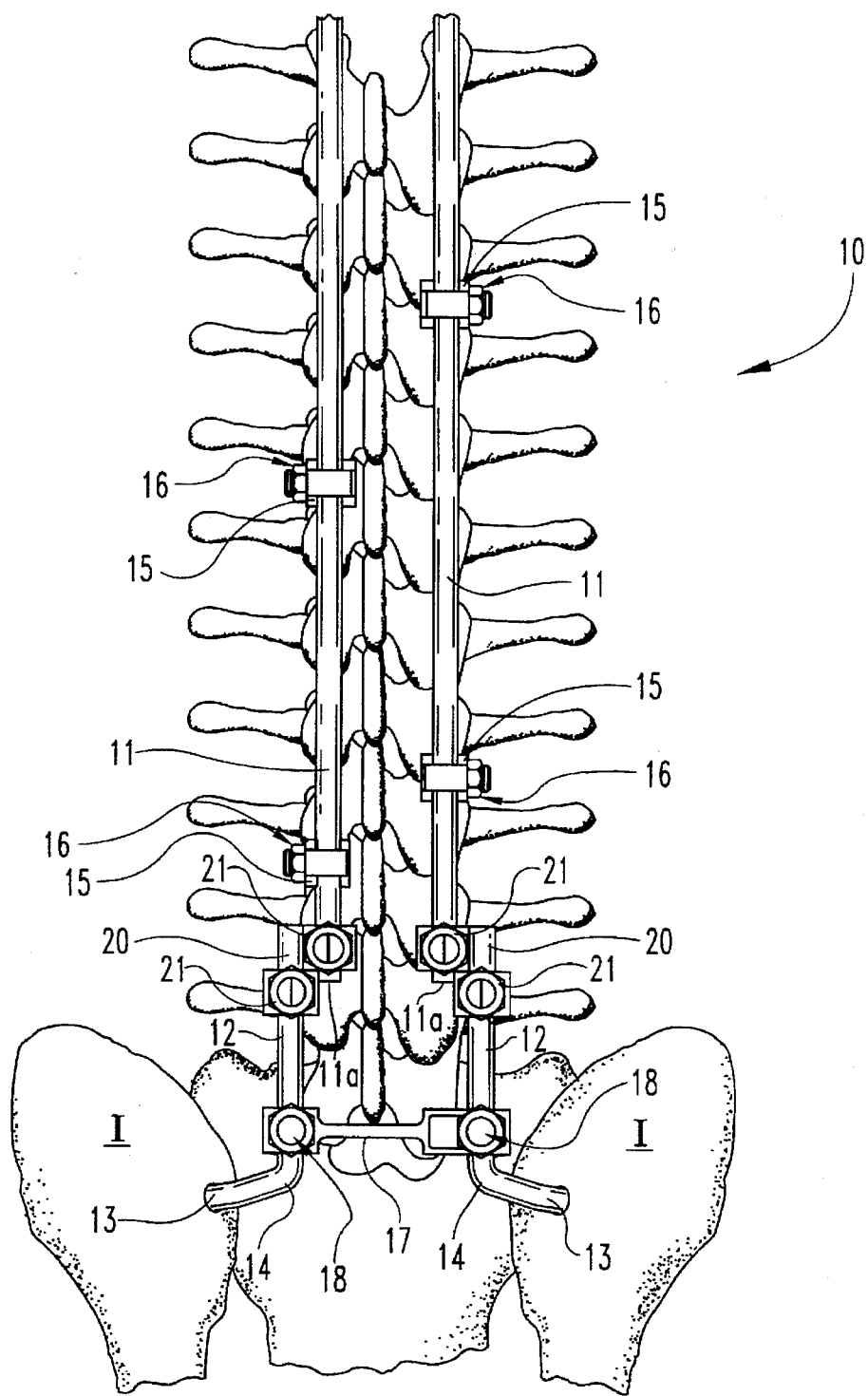
FIG. 1 is a top elevational view of a spinal fixation construct in accordance with one prior art system.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
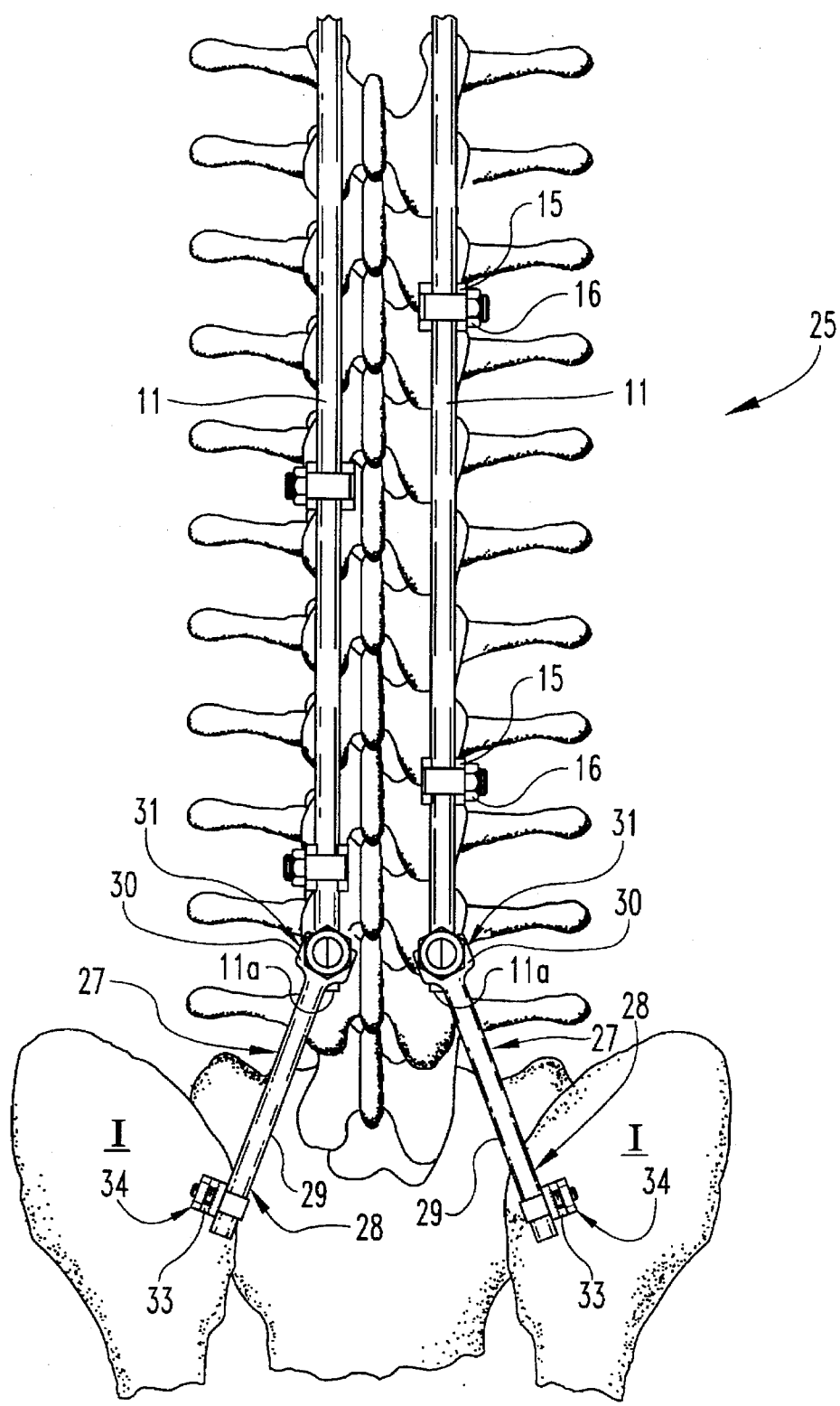
FIG. 2 is a top elevational view of a spinal fixation system utilizing a variable angle extension rod assembly in accordance with one embodiment of the present invention.
Figure 3:
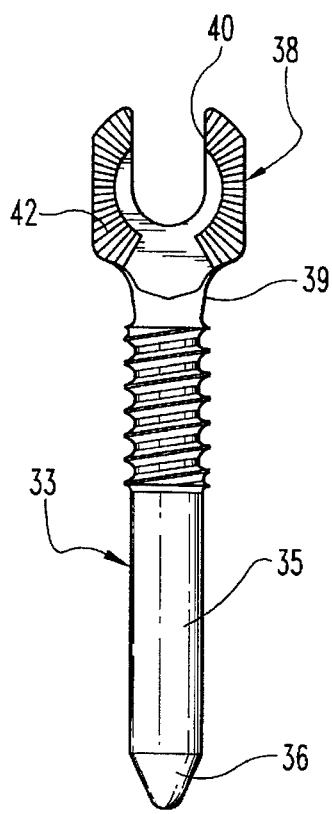
FIG. 3 is a top elevational view of an iliac screw used with the variable angle extension rod assembly shown in FIG. 2.
Figure 4:
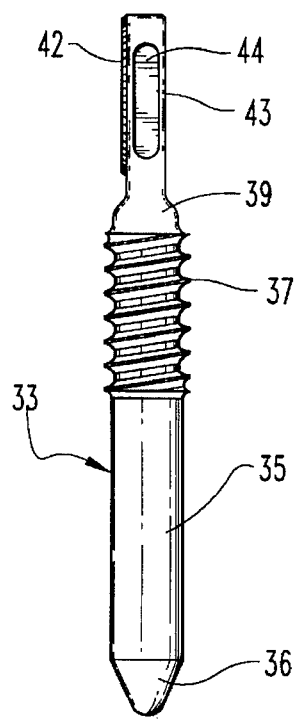
FIG. 4 is a side elevational view of the iliac screw shown in FIG. 3.

One embodiment of an iliac bone screw 33 of this invention is shown in FIGS. 3 and 4. In particular, the bone screw 33 is configured for engagement into the iliac wings I (FIG. 2). The bone screw includes a smooth shank 35 preferably terminating in a blunt tip 36. The screw 33 also includes a proximal threaded shank 36 adjacent the smooth shank 35. The proximal end of the iliac screw bears a head portion 38, with a transition region 39 provided between the cylindrical threaded shank 36 and the generally flat head portion 38.

In one preferred embodiment, the smooth shank 35 has a length that is about 2–3 times greater than the length of the proximal threaded shank 37. The smooth shank is adapted to penetrate the soft cancellous bone of the iliac wings I. The tip 36 of the distal shank 35 is blunt to reduce the risk that the iliac screw will pass through cortical bone on the opposite side of the iliac wing I. In addition, the blunt tip makes insertion of the screw safer and generally easier, since in one preferred method for insertion, the iliac screw is pushed directly into the iliac wings, pushing aside the cancellous bone as the screw is pushed deeper into the iliac bone.

Preferably, the threads of the proximal threaded portion 37 are configured to engage both the cancellous bone and the harder cortical bone. In a preferred embodiment, the threads have a diameter of about 9 mm and have a sufficient length to engage both cortical and cancellous bone. In one specific embodiment, the proximal threaded shank 37 has a length of about 20 mm to provide adequate purchase in both types of bone.

Again in the preferred embodiment depicted in FIGS. 3 and 4, the head portion 38 permits variable angle attachment to an elongated rod such as the extension rod 27 shown in FIG. 2. The head portion preferably includes a slot 40 for seating an eyebolt stem 47. The head portion 38 also includes a radially splined surface 42 and an opposite smooth surface 43. The sides of the head portion 38 are most preferably provided with holding instrument recesses 44 which are configured to be grasped by a conventional gripping tool such as a hook or screw holder. The gripping tool is used to implant the screw 33 and provide whatever driving force is necessary to push the smooth shank 35 into the cancellous bone and to thread the proximal threaded shank 37 into the cortical and cancellous bone.

Figure 6:
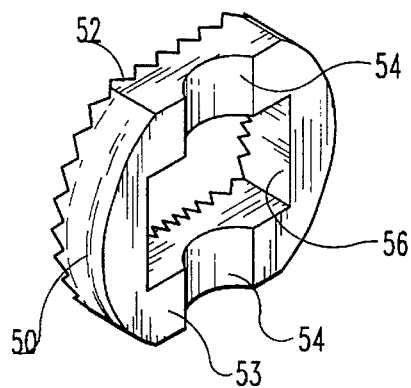
FIG. 6 is an enlarged perspective view showing a washer used with the clamping member depicted in FIG. 5.
Figure 5:
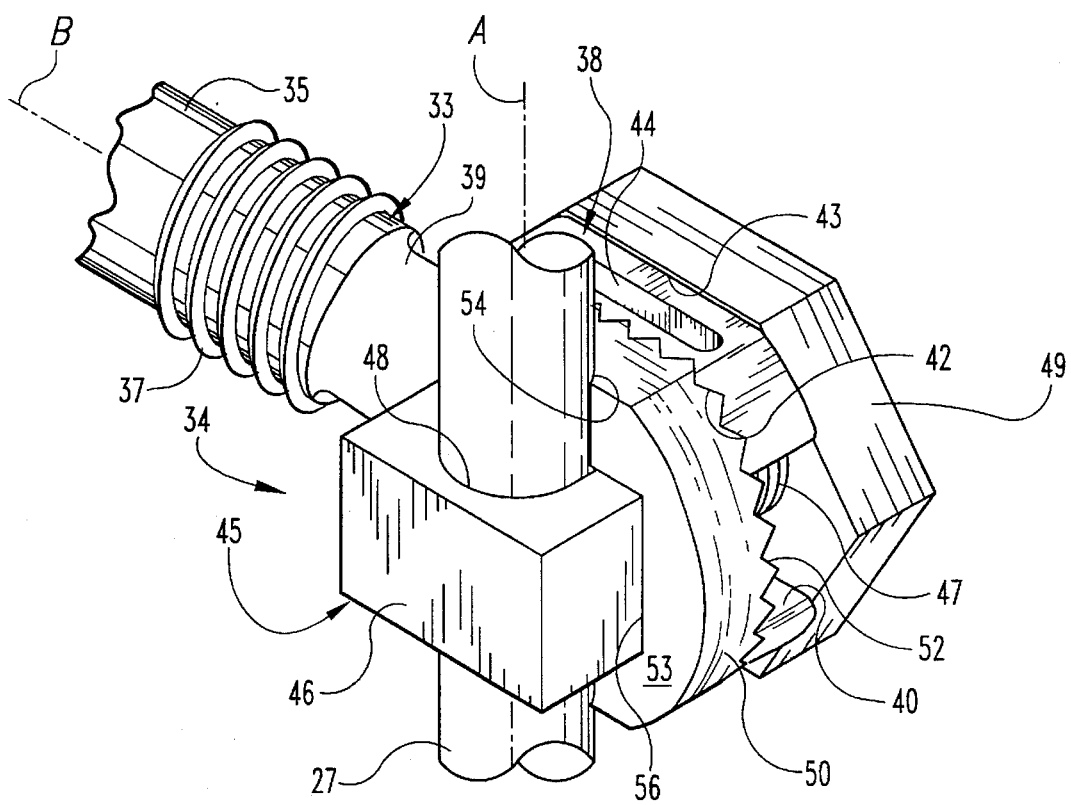
FIG. 5 is an enlarged detailed perspective view showing a clamping member used to engage the iliac screw to the variable angle extension rod assembly shown in FIG. 2.

The details of the variable angle connection of the iliac screw 33 with an extension rod 27 are shown in FIGS. 5 and 6. In particular, the clamping assembly 34 includes an eyebolt 45 formed by a body 46. The eyebolt 45 includes a threaded stem 47 projecting from the body 46 which is adapted to engage a threaded nut 49. The eyebolt body 46 further defines an aperture 48 through which the rod 27 extends.

In a further aspect of the clamping member 34, a washer 50 is preferably disposed between the rod 27 and the head portion 38 of the screw 33. The washer 50 includes a mating surface 52 which mates with the surface 42 of the iliac screw 33. Preferably, the washer mating surface 52 is correspondingly splined so that the splines between the washer and the bone screw head portion interdigitate. This interdigitation permits variable angular orientations of the head portion 38 of the bone screw 33 relative to the washer 50.

The washer also preferably includes an opposite rod contact surface 53 which defines a groove 54. The groove 54 has a diameter that will receive the rod 27 therein. Most preferably, in accordance with the TSRH® three point shear clamp philosophy, the groove 54 has a radius slightly smaller than the radius of the rod 27. The washer 50 further includes an eyebolt opening 56 which is configured to fit over the body 46 of the eyebolt 45. In the preferred embodiment, the eyebolt body 46 is rectangular so that the eyebolt opening 56 is also rectangular. As assembled, the washer 50 overlaps a portion of the eyebolt body when the rod 27 is received within the groove 54.

As shown in FIG. 5, the manner in which the iliac screw 33 is engaged to the rod 27 by way of clamping member 34 is depicted. In particular, it can be seen that the eyebolt 45 is first disposed on the rod 27 with its threaded stem 47 projecting outward or laterally (see FIG. 2). The washer 50 is then placed over the threaded stem 47 with the eyebolt body 46 positioned within the eyebolt opening 56. The washer 50 is situated with the groove 54 contacting the rod 27 and with the splined mating surface 52 facing outward away from the rod. The head portion 38 of the screw 33 is then brought into contact with the washer 50, and particularly with its radial splined surface 42 interdigitating with the mating surface 52 of the washer. The nut 49 can then be threaded onto the threaded stem 47 of the eyebolt 45 to clamp the entire assembly together.

Until the nut 49 is tightened onto the eyebolt, the angular and translational relationship between the iliac screw 33 and the rod 27 can be changed. In particular, the eyebolt 45 can be rotated about the longitudinal axis A of the rod 27 and can be translated in a direction parallel to the axis A. Further, the angle between the longitudinal axis B of the iliac screw 33 and the axis A of the rod 27 can be varied as necessary to engage the screw to the rod when the screw is already embedded within the iliac wing I. These three degrees of adjustment avoid the need to bend the extension rod 27 and allow the surgeon great flexibility in the placement of the iliac screw 33 within the iliac wings I.

In a preferred method for implanting the bone screw 33, only minimal preparation of the iliac bone site is necessary. In one embodiment, a blunt probe can be pushed into the iliac wings to produce a "starter" hole for the bone screw. The probe preferably has a diameter much smaller than the diameter of the bone screw. In one specific embodiment, the smooth shank 35 of the bone screw 33 has a diameter of 8 mm, so that a blunt probe of about 4 mm would be acceptable for generating the starter hole. Once the starter hole has been made, the bone screw 33 can then be directly inserted into the iliac wing I simply by pushing the smooth shank 35 into the opening. Once the proximal threaded shank 37 contacts the iliac bone, the holding instrument can be used to rotate the screw 33 to engage the threads within the cortical and cancellous bone.

Alternatively, the cortical bone can be removed to facilitate insertion of the screw 33. This removal can be accomplished by drilling or by performing an osteotomy. In either case, the proximal threaded shank 37 would simply engage the cancellous bone to prevent pull out and to avoid the windshield wiper phenomenon associated with prior Galveston rods.

In a further embodiment of the method of use of the iliac screw 33, the screw can be used to bridge the sacro-iliac joint between the iliac wing and the sacrum. Bridging this joint adds much greater rigidity to the construct to help fusion in the superior vertebral levels. One benefit accomplished by this iliac screw 33 is that it can be subsequently removed once the superior instrumented vertebral levels have fused. This can be accomplished by simply loosening the nut 49 from the stem 47 of the eyebolt 45 and moving the eyebolt away from the head portion 38 of the bone screw 33. The same holding instrument used to insert the screw can then be used to unthread the proximal threaded shank 37 and pull the smooth shank 35 out of the iliac bone.

Figure 7:
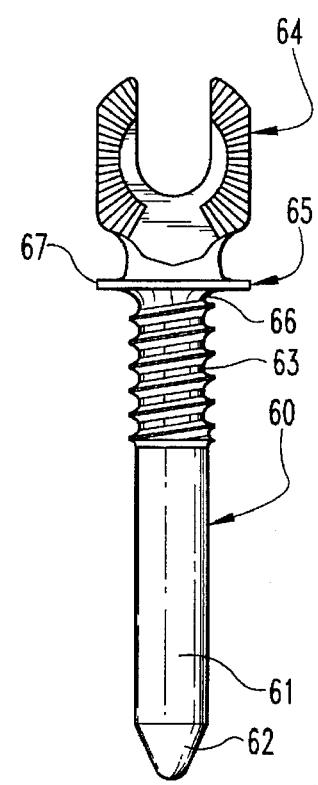
FIG. 7 is a top elevational view showing a further embodiment of the iliac screw in accordance with the present invention.

A further embodiment of the invention is depicted in FIG. 7. The bone screw 60 includes a smooth shank 61 having a blunt tip 62 and a proximal threaded shank 63. The bone screw also includes a head portion 64, with each component thus far described being substantially similar to the corresponding components of the bone screw 33. The principal difference in this embodiment is that the transition region 67 is modified to include a flare 66 from the threaded shank 63. This flare 66 leads to a shoulder 67 which has a diameter greater than the diameter of the threaded shank 63. This shoulder 67 can provide a support for other spinal components and can also serve as a stop to prevent over-insertion of the bone screw 60 into the iliac bone.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

For example, the variable angle capability of the iliac screw 33 can be achieved with the radial splines described above. This radial spline arrangement is also discussed more fully in U.S. Pat. No. 5,261,909 showing a variable angle screw for a spinal implant system. However, other surface features are contemplated which permit variable relative angular orientations between the clamping member and the extension rod of the extension rod assembly. For instance, certain knurling patterns can permit variable angular relationships between the two components.

In the preferred embodiment, the elements of the spinal fixation system, and particularly of the iliac screw 33, are formed of a medically biocompatible material, such as 316 LVN stainless steel; however, other materials such as titanium are contemplated. The bone screw 33 is sized according to the anatomy of the iliac wings or the sacro-iliac joint. Preferred lengths range between 70–100 mm while the diameter of the smooth and threaded shanks can be 8–9 mm for secure purchase in the iliac bone.

What is claimed:

1. A bone screw for connection between a human bone and a fixation member comprising:
   a smooth distal shank terminating in a smooth tip at a distal end of said bone screw;
   a threaded proximal shank carrying bone engaging threads; and
   a head portion adjacent said proximal shank at an opposite proximal end of said bone screw, said head portion being configured for engagement to the fixation member.

2. The bone screw according to claim 1, wherein said smooth distal shank has a first length, said proximal threaded shank has a second length, and said first length is greater than said second length.

3. The bone screw according to claim 2, wherein said first length is about 50 mm and said second length it about 20 mm.

4. The bone screw according to claim 2, wherein said first length is at least twice as long as said second length.

5. The bone screw according to claim 1, wherein said bone engaging threads are cancellous threads.

6. The bone screw according to claim 1, wherein said tip at said distal end of said bone screw is blunt.

7. The bone screw according to claim 1, wherein said head portion includes a surface carrying radial splines.

8. The bone screw according to claim 1, wherein said head portion defines a slot, said slot open at said proximal end of said bone screw to receive a clamping member therein.

9. The bone screw according to claim 1, wherein said head portion defines a pair of recesses configured for engagement by a gripping tool for insertion of said bone screw into the human bone.

10. The bone screw according to claim 1, further comprising a transition region between said threaded proximal shank and said head portion, said transition region including a shoulder having an outer diameter larger than an outer diameter of said threaded proximal shank.

11. The bone screw according to claim 1, wherein said proximal threaded shank has a maximum diameter greater than a maximum diameter of said smooth distal shank.

12. The bone screw according to claim 11, wherein said head portion defines a slot open at said proximal end and includes a surface defining a plurality of radially spaced apart splines.

13. The bone screw according to claim 1, wherein said smooth distal shank has a diameter approximately equal to a root diameter of said threaded proximal shank.

14. A spinal fixation system comprising:
  an elongated spinal member sized and configured to extend longitudinally along a length of the spine, said spinal member having an inferior end disposable adjacent an iliac wing;
  a plurality of bone engaging members engageable to the spine;
  a corresponding plurality of first clamping members for engaging said plurality of bone engaging members to said elongated spinal member;
  an iliac screw configured for engagement within the iliac wing, said iliac screw including;
  a smooth distal shank at a distal end of said bone screw;
  a threaded proximal shank carrying bone engaging threads; and
  a head portion adjacent said proximal shank at a proximal end of said bone screw; and
  a second clamping member for clamping said head portion of said iliac screw to said elongated spinal member.

15. The spinal fixation system of claim 14, wherein:
  said second clamping member includes an eyebolt defining an aperture for receiving said elongated spinal member therethrough, a threaded stem and a threaded nut engageable on said stem; and
  said head portion of said iliac screw defines a slot for receiving said threaded stem of said eyebolt therein, a first surface facing said elongated spinal member and a second surface opposite said first surface for contact with said threaded nut when said nut is engaged on said threaded stem.

16. The spinal fixation system of claim 14, wherein:
  said head portion of said iliac screw includes a first mating surface and said second clamping member includes a second mating surface, and said first and second mating surfaces are configured to interdigitate with each other to permit variable angular positions of said head portion relative to said second clamping member.

17. The spinal fixation system of claim 16, wherein:
  said second clamping member includes an eyebolt defining an aperture for receiving said elongated spinal member therethrough, a threaded stem, a threaded nut engageable on said stem, a washer having said second mating surface and an opening sized to receive said eyebolt therethrough; and
  said head portion of said iliac screw defines a slot for receiving said threaded stem of said eyebolt therein, said first mating surface of said head portion facing said washer and a contact surface opposite said first mating surface for contact with said threaded nut when said nut is engaged on said threaded stem.

18. The spinal fixation system of claim 14, wherein said proximal threaded shank has a maximum diameter greater than a maximum diameter of said smooth distal shank.

19. The bone screw according to claim 14, wherein said smooth distal shank has a diameter approximately equal to a root diameter of said threaded proximal shank.

* * * * *